United States Patent [19]

Dewhirst

[11] Patent Number: 4,861,810
[45] Date of Patent: Aug. 29, 1989

[54] NEW RESIN MATERIALS BASED ON AMINES

[75] Inventor: Kenneth C. Dewhirst, Houston, Tex.

[73] Assignee: Shell Oil Company, Houston, Tex.

[21] Appl. No.: 233,863

[22] Filed: Aug. 15, 1988

Related U.S. Application Data

[63] Continuation of Ser. No. 871,950, Jun. 9, 1986, abandoned.

[51] Int. Cl.$^4$ ............................................. C08G 59/50
[52] U.S. Cl. .................................... 523/445; 523/466; 523/468; 525/423; 525/523; 525/528; 528/104; 528/121; 528/122; 528/124; 528/407
[58] Field of Search ....................... 523/445, 466, 468; 525/423, 523, 528; 528/104, 121, 122, 124, 407

[56] References Cited

U.S. PATENT DOCUMENTS

| | | | |
|---|---|---|---|
| 3,306,872 | 2/1967 | Maycock et al. | 260/32.8 |
| 3,454,670 | 7/1969 | Cantatore et al. | 528/121 X |
| 3,546,165 | 12/1970 | Morgan | 260/47 |
| 3,592,946 | 7/1971 | Griffith | 528/121 |
| 3,637,590 | 1/1972 | Maycock et al. | 260/47 EP |
| 3,821,162 | 6/1974 | Dexter | 260/45.8 N |
| 4,201,854 | 5/1980 | Zondler et al. | 528/121 |
| 4,308,085 | 12/1981 | Hörhold et al. | 528/121 X |
| 4,473,674 | 9/1984 | Stoakley et al. | 523/454 |
| 4,684,678 | 8/1987 | Schultz | 523/466 |

FOREIGN PATENT DOCUMENTS

| | | |
|---|---|---|
| 2142579 | 9/1972 | Fed. Rep. of Germany . |
| 209358 | 4/1984 | German Democratic Rep. . |
| 211799 | 7/1984 | German Democratic Rep. . |

OTHER PUBLICATIONS

Kourtides et al., "Advanced Thermoset Resins for Fire-Resistant Composites". 11th Nat. SAMPE Technical Conference, p. 551–563 (1979).
"Fire-Resistant Composites", NASA Tech. Briefs. Spring 1983, p. 285.
J. F. McGrath, 29th National SAMPE Synposium, Apr. 3–5, 1984, p. 447–458.
Bell, James P., *J. Polymer Science*, A2, 6, pp. 117–136 (1970).

*Primary Examiner*—Earl Nielsen
*Attorney, Agent, or Firm*—Dean F. Vance

[57] ABSTRACT

The present invention relates to a new thermoplastic polymer composition having the processing characteristics of a thermosetting polymer along with an improved balance of properties including improved modulus/glass transition temperature/toughness balance. These new polymer compositions are prepared by reacting certain amine compounds with certain diepoxide compounds to form linear units which are lightly cross-linked. Also disclosed and claimed are processes for preparing such compositions, cured compositions and end-use applications.

87 Claims, No Drawings

NEW RESIN MATERIALS BASED ON AMINES

This is a continuation of application Ser. No. 871,950 filed June 9, 1986, now abandoned.

FIELD OF THE INVENTION

The present invention relates to novel and unobvious compositions which may be fabricated into termoset composite structures by typical thermosetting resin methods. In particular, the present invention relates to lightly crosslinked compositions having flexible portions and bulky stiff portions, prepared by reacting a polyepoxide with certain amines to form linear molecules and lightly crosslinking the resulting linear molecules.

BACKGROUND OF THE INVENTION

Epoxy compositions and their curing techniques are well known, and the patents issued on curable epoxy compositions number in the hundreds. It will be appreciated that each and every one of the known epoxy-curing systems exhibits advantages over other systems, and, as importantly, disadvantages over the same systems. There is, of course, a continuing need to develop better epoxy compositions.

There is, in particular, an increasing need in the aerospace and automotive sectors for high performance thermosetting compositions or matrices for fiber reinforced composites. Fiber reinforced composites are very desirable in aerospace applications because they can offer a combination of good stiffness, strength and are light weight. Increasingly, the aerospace manufacturers have demanded *higher* performance from the thermoset resins used in fiber reinforced composites. These higher performance thermoset resins are expected to possess these following characteristics:
- good mechanical properties at temperatures above about 90° C.
- good thermal oxidative stability
- good toughness properties, including good impact resistance
- good fatigue properties
- good chemical and solvent resistance
- good fire resistance
- high resistance to humidity, e.g., the "hot-wet" properties of the composite must remain high.

A further, and very important property of such systems is that the composite must have acceptable processing characteristics. For example, the current techniques for manufacturing aerospace components typically involves the use of prepregs and laminates, which are cured by applying heat and pressure in a vacuum bag/autoclave-type apparatus. Therefore, the most desirable thermosetting resin compositions should be processable on the standard equipment currently utilized in the aerospace industry.

A broad spectrum of thermosetting epoxy resin systems is currently being used by the aerospace industry, primarily as composite matrices and adhesives. As a class, epoxy resin systems are very versatile materials offering, as mentioned above, chemical resistance, high adhesive strength, good electric properties and are easy to use or process into composites. However, to improve their high temperature properties, such current epoxy resin systems must be highly crosslinked. This crosslinking, however, results in generally lower toughness.

There are currently various engineering thermoplastics (not thermosetting polymers) that offer excellent high temperature properties along with high toughness. One such example currently being investigated is the use of poly(ether-ether)ketone ("PEEK") as the matrix. However, there are processing problems with the use of PEEK and other similar engineering thermoplastic resins since such materials not only are difficult to process on thermoplastic apparatus (i.e., difficult to extrude), but also do not lend themselves to processing by the thermosetting techniques now currently in use by the aerospace industry.

What is needed is a resin system that not only combines the good property advantages of such high performance engineering thermoplastics such as PEEK, but is also processable as a thermosetting resin matrix.

DESCRIPTION OF THE PRIOR ART

Thermoplastic polyethers having relatively high impact strength are disclosed and claimed in U.S. Pat. No. 3,637,590, while the process for preparing such polymers is claimed in U.S. Pat. No. 3,306,872. Even though such polymers, which are based on the reaction product of certain diepoxides with certain bisphenols, have improved impact strength, such polymers lack adequate high temperature properties and solvent resistance for high performance applications. Similar compositions having improved impact strength are also disclosed in Fed. Rep. of Germany OLS No. 2,142,579 where certain diepoxides are reacted with certain diphenols (e.g. 2,2-bis(4-hydroxynaphth-1-yl)propane) to produce polymers for eyeglasses.

Thermosetting resins having improved performance characteristics are disclosed in the article "Advanced Thermoset Resins for Fire-Resistant Composites", by Kourtides et al, 11th National SAMPE Technical Conference, pages 551–563 (1979). While the thermoset resins disclosed therein, such as the epoxy resins based on the diglycidyl ether of bisphenol A and the diglycidyl ether of bisphenol fluorenone, have improved high temperature properties, they also lack adequate toughness for truly high performance applications. See also Fire-Resistant Composites, NASA Tech Briefs, Spring 1983, p. 285.

Other epoxy systems such as those disclosed in U.S. Pat. No. 4,473,674, are touted for aerospace applications. The composites described in the '674 patent are based on multifunctional epoxies, such as tetraglycidylmethylenedianiline cured with DDS. Such systems also have important deficiencies as discussed in the various examples which follow.

Epoxy-amine addition polymers are described in a number of patents and publications, including by way of example only, Horhold et al, High Molecular Weight Linear Epoxy-Amine Addition Polymers, Z. Chem., Vol. 22, No. 5, 1982, pp. 166–176; DDR Patentschrift 211,799; and DDR Patentschrift 209,358.

New compositions having improved properties are herein claimed.

SUMMARY OF THE INVENTION

The present invention relates to a composition having the processing characteristics of a thermosetting polymer along with an improved balance of properties including solvent resistance and improved modulus/glass transition temperature/toughness balance. In particular the present invention relates to a polymer composition comprising lightly crosslinked linear molecules having the repeating structures prior to crosslinking of the general formula:

$$-[A-CH_2-CH(OH)-CH_2-B-CH_2-CH(OH)-CH_2]-$$

where A is selected from the group consisting of:

$$-\overset{X}{N}-, \quad -\overset{Y}{N}-, \quad -\overset{R'}{N}-X-\overset{R}{N}-, \quad -\overset{R'}{N}-Y-\overset{R}{N}$$

and mixtures thereof, and B is selected from the group consisting of:

$$-O-X-O, \quad O-Y-O, \quad -\overset{X}{N}-, \quad -\overset{Y}{N}-, \quad -\overset{R'}{N}-X-\overset{R}{N}-,$$

$$-\overset{R'}{N}-Y-\overset{R}{N}-$$

where R and R' are selected from the group consisting of unsubstituted or inertly substituted $C_1$-$C_{20}$ aliphatic, cycloaliphatic or aromatic hydrocarbyl groups, and wherein said repeating structures are lightly crosslinked such that between 1 and 50 of said repeating structures per 100 total repeating structures are crosslinked to repeating structures of other molecules, and where:

(a) "X" represents a stiff segment comprising stiff units (SU) and optional flexible units (FU), which stiff units and flexible units are interconnected;

(b) "Y" represents a flexible segment comprising stiff units (SU') and optional flexible units (FU') which stiff units and flexible units are interconnected;

(c) said stiff units, SU and SU', are independently selected from the group consisting of substituted and non-substituted aromatic rings, cycloaliphatic rings and non-interfering heterocyclic rings;

(d) said flexible units, FU and FU', are independently selected from the group consisting of $$-\overset{|}{\underset{|}{C}}-, \quad \diagup\overset{|}{N}\diagdown, \quad \diagup O \diagdown, \quad -\overset{|}{\underset{|}{Si}}-, \quad \diagup B \diagdown \text{ and } \diagup S \diagdown;$$

(e) the number of stiff segments in the resulting polymer compositions is "a", the number of flexible segments in the resulting polymer compositions is "b", and the ratio of $$\frac{a}{a+b}$$

is less than or equal to one; and (f) the ratio of the number of stiff units to flexible units in said stiff segment (SU/FU) is equal to or greater than the ratio of the number of stiff units to flexible units in said flexible segment (SU'/FU').

Also disclosed and claimed herein are compositions containing fibrous reinforcing materials, prepregs prepared from such reinforced compositions and articles prepared from such prepregs.

ADVANTAGES AND OBJECTS OF THE PRESENT INVENTION

One object of the present invention is to produce compositions having the processing characteristics of thermosetting polymers, while also having the high performance characteristics of premium thermoplastic polymers.

Another object of the present invention is to tailor make polymers for particular applications, i.e., to design polymers having the required balance of solvent resistance, thermal properties, mechanical properties and toughness for the specific application end use.

Still another object of the present invention is to prepare fiber reinforced composites having particular utility in aerospace applications.

Still another object of the present invention is to prepare fiber reinforced composites having a desired balance of tack and drape.

Still other objects and advantages will be apparent from the application.

As shown in the examples which follow, applicant has discovered a new method for preparing novel polymers wherein it is now possible to obtain both high temperature performance and high toughness, i.e., applicant has discovered a means to uncouple the usual temperature/toughness balance relationship. In particular, in a preferred embodiment applicant has prepared polymers having the following property set:

Glass transition temperature, $T_g$ = 168° C.(*DSC*)

Fracture toughness, $K_q$ = 2.3 *KSI* $\sqrt{in}$ (Compact Tension)

Fracture modulus, $E$ = 520 *KSI* (Dry @ *R.T.*)
490 *KSI* (Wet @ 200° F.)

Water gain, $\Delta W/W_o$ = 0.8% (saturation)

DETAILED DESCRIPTION OF THE INVENTION

There are two basic aspects to the present invention—one involves the process for making certain compositions and the other involves the polymers as compositions-of-matter.

I. PROCESS

In the broad sense, the present invention relates, as a minimum, to the mixture of an amine component and a diepoxide component to make a prepolymer composition, which may be stored for later reaction or which may be reacted with a condensation catalyst.

A. Amine Component

The amine component employed in making the polymers of the present invention is selected from the group consisting of primary amines, bis secondary amines and mixtures thereof.

The primary amines will have the general formula $$\overset{X}{\underset{H\diagup \diagdown H}{N}} \quad \text{or} \quad \overset{Y}{\underset{H\diagup \diagdown H}{N}}$$

or a mixture thereof where "X" and "Y" are the stiff segments or flexible segments referred to before.

The bis secondary amines will have the general formula:

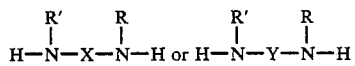

or a mixture thereof where "X" and "Y" are the stiff segments or flexible segments referred to before and R and R' are unsubstituted or inertly-substituted $C_1$–$C_{20}$ aliphatic, cycloaliphatic or aromatic hydrocarbyl groups. Preferably R and R' are $C_1$–$C_{10}$ alkyl groups. Examples of R and R' include methyl, ethyl, isopropyl, cyclohexyl, benzyl, tolyl and the like.

Examples of primary monoamines include aniline (phenylamine), 2,6-dimethylaniline, 2,4-dimethylaniline, 2,6-diethylaniline, N-aminophthalimide, 2,6-diisopropylaniline, tolylamine, α-naphthylamine, 3-aminobenzothiophene, 1-aminoadamantane, and norbornylamine. Preferred primary monoamines include aniline, 2,6-dimethylaniline and 2,6-diethylaniline with 2,6 diethyl aniline being most preferred.

Examples of bis secondary amines include N,N'-dimethyl-p-phenylenediamine, N,N'-dicyclohexyl-p-phenylenediamine, bis-(N-sec-butyl-4-aminophenyl)methane, α,α'-bis(N-sec-butyl-4-aminophenyl)-p-diisopropylbenzene, 9,9-bis-(N-methyl-4-aminophenyl)fluorene, N,N'-dimethyl-4,4'-diaminodiphenyl sulfone, and α,α'-bis(1-hydroxy-2-napthyl)-para-diisopropylbenzene.

Regarding specific examples of suitable diamines, reference can be made to East German published patent application DD 211799 and the article by Horhold et al titled High Molecular Weight Linear Epoxy-Amine Addition Polymers, Z. Chem., Vol. 22, No. 5, 1982, pp. 166–176.

In a broad sense, one important aspect of the present invention is the selection of stiff units and flexible units such that the resulting polymer molecules have the appropriate type and ratio of stiff units to flexible units.

By use of the term "flexible units" are meant those units that permit rotation at an angle. Examples of such flexible units are Broad group    Examples

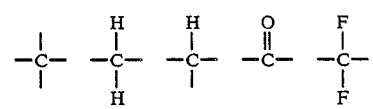

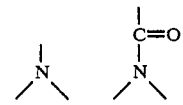

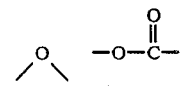

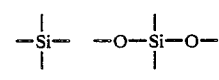

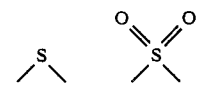

The stiff units are selected from the group consisting of substituted or non-substituted aromatic rings, cycloaliphatic rings and heterocyclic rings. The aromatic rings are inertly substituted or un-substituted benzene radicals. Substituted benzene radicals have substituents which do not interfere in the process, independently selected from the group consisting of Cl, Br or $C_1$–$C_5$ alkyl groups. Annulation of benzene rings gives rise to

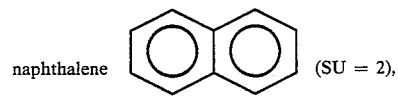

naphthalene (SU = 2),

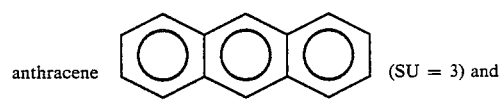

anthracene (SU = 3) and

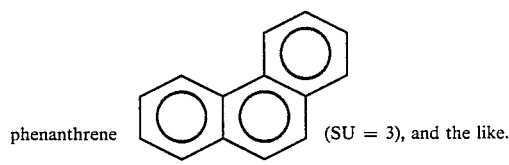

phenanthrene (SU = 3), and the like.

The cycloaliphatic rings are substituted or un-substituted $C_5$ or $C_6$ hydrocarbon radicals. Substituted cycloaliphatic rings are analogous to substituted aromatic rings. Un-substituted rings include, by way of example, cyclopentane, cyclohexane and cyclohexene. Annulation of cycloaliphatic rings gives rise to

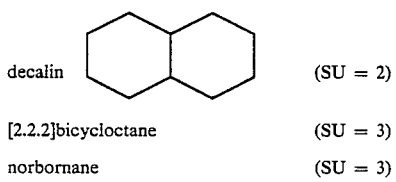 decalin (SU = 2)

 [2.2.2]bicyclooctane (SU = 3)

norbornane (SU = 3)

adamantane (C₁₀H₁₆) (SU = 4) and the like.

The term heterocyclic rings refers to substituted or un-substituted 5-6 membered heterocyclic radicals. Examples of 5-6 membered heterocyclic radicals are radicals of

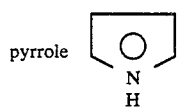 pyrrole

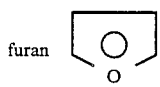 furan

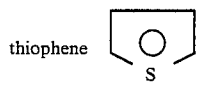 thiophene

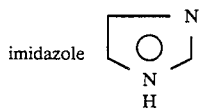 imidazole

 oxazole

 thiazole

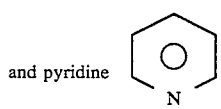 and pyridine

Annulation of heterocyclic rings with aromatic rings give rise to

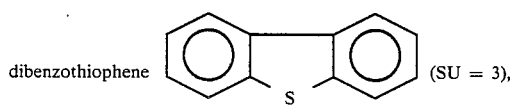 dibenzothiophene (SU = 3),

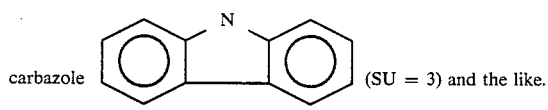 carbazole (SU = 3) and the like.

Regarding the selection of heterocyclic structures, O and S heterocycles are generally suitable. In the case of N derivatives, however, care must be exercised such that the N is not strongly basic so that homopolymerization of the epoxide occurs. For example,

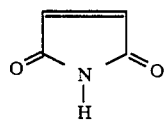

is suitable, but

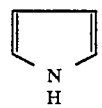

may not be suitable by itself (however the carbazole analog is suitable since the N is not strongly basic there).

B. Diphenol Component

A portion, e.g. about one mole percent to about 99 mole percent, of said amine component can be replaced with a diphenol component. Preferably, when this replacement is desired, about 25 to about 75 mole percent of said amine component is replaced with said diphenol component.

In a preferred embodiment the diphenol components employed herein have the structure HO-X-OH or HO-Y-OH where "X" represents the stiff segment specified above and "Y" represents the flexible segment specified above.

One group of diphenol components particularly useful herein are those mentioned in U.S. Pat. No. 3,546,165. Specifically, those useful components are those phenoxy compounds of the formula

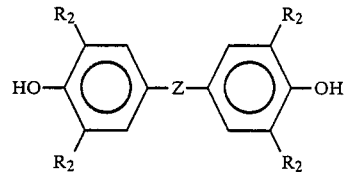

where each $R_2$ substituent is independently selected from H, Cl, Br or $C_1$-$C_5$ alkyl and Z is a substituent having flexible units (FU or FU') and stiff units (SU or SU') where Z represents a gem-bivalent radical having 1 to 2 aromatic hydrocarbon rings and a gem-bivalent non-aromatic ring selected from the group consisting of a ring of 5 carbon atoms, a ring of 6 carbon atoms one of which carbon atoms may bear an oxo oxygen atom, and a ring of 5 carbon atoms and one oxygen atom, said gem-bivalent non-aromatic ring being fused to said aromatic hydrocarbon rings. Particularly useful are those components where Z is

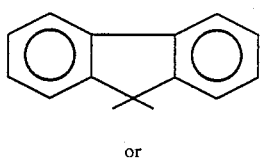

or

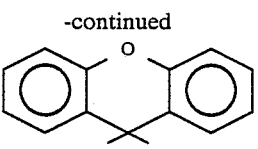

Specific examples include the following bisphenols:
9,9-bis(4-hydroxyphenyl)fluorene,
1,1-bis(4-hydroxyphenyl)-indane,
9,9-bis(4-hydroxyphenyl)xanthene,
10,10-bis(4-hydroxyphenyl)anthrone,
9,9-bis(4-hydroxyphenyl)phenanthrone.
Other useful bisphenols include phenolphthalene,
9,9-bis(4-hydroxyphenyl)-9,10-dihydroanthracene,
9,9-bis(4-hydroxyphenyl)-10,10-diphenyl-9,10-dihydroanthracene,
3,3-bis(4-hydroxyphenyl)-4,5-benzodihydrofuran, and the like.

Another group of diphenol components useful herein are the imides represented by the formula

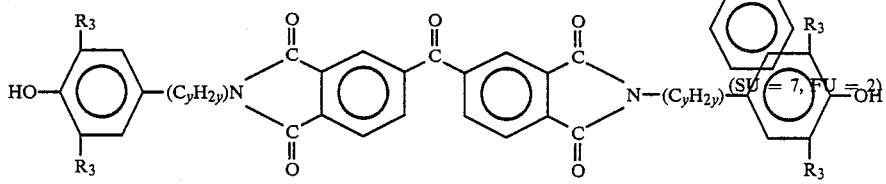

wherein each of $R_3$ is the same or different (lower) alkyl group of from one to four carbon atoms; and y has a value of from 0 to 3. Such diphenol compounds are disclosed in U.S. Pat. No. 3,821,162 and reported by J. E. McGrath, 29th National SAMPE Symposium, Apr. 3-5, 1984, page 447.

Still another group of diphenol compounds are those based on phthalocyanine. Such compounds include the following:

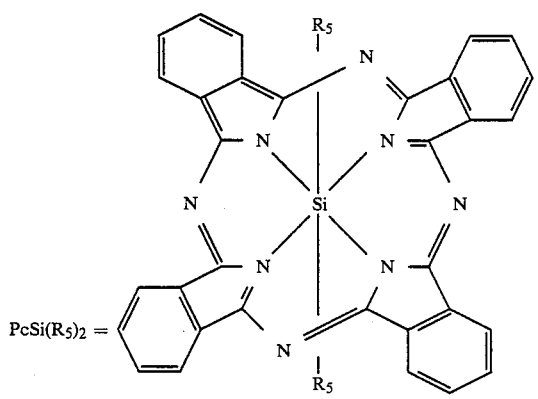

(a) $R_5$ = OH

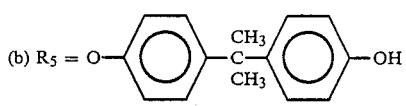

(b) $R_5$ = O—

Still another group of diphenol compounds are those shown below. Additional aromatic, cycloaliphatic or heterocyclic rings may be annulated as desired:

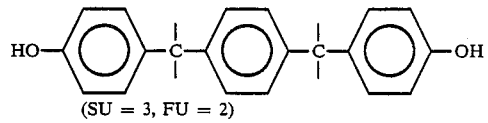

(SU = 3, FU = 2)

(SU = 5, FU = 2)

(SU = 7, FU = 2)

This particular group of diphenol compounds is distinguished from diphenol compounds such as BPA and the like, by the presence of 2 or more flexible units

If desired, the diphenoxy compounds described above may be substituted in part (or even in whole in certain cases) with other diphenols, represented by the general formula

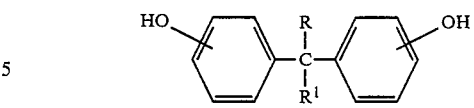

in which R and $R^1$ when taken collectively with the connector carbon C are selected from the group consisting of cyclohexyl and alkyl-substituted cyclohexyl, and when taken separately are from the group consisting of hydrogen, alkyl, cyclohexyl, phenyl, alkyl-substituted cyclohexyl, alkyl substituted phenyl, halogen substituted cyclohexyl and halogen substituted phenyl groups with the total number of carbon atoms in the group or groups attached to said connector carbon atom not exceeding eighteen and the number of carbon atoms in any of said alkyl substituent groups not exceeding six.

The preferred phenols have the hydroxyl groups in the 4,4' positions, but compounds with hydroxyls in the 2,2', 3,3', 2,4', and other arrangements may also be used. R and $R^1$ suitable are methyl, ethyl, isobutyl, n-nonyl, n-heptadecyl and the like. Other dihydric phenols may also be employed, excepting those which have two hydroxyl groups in ortho positions on a single benzene ring.

The dihydric phenol employed in the process of this invention may be substantially 100 percent pure, or may be a technical grade of somewhat lower purity. Concentrates of dihydric phenols containing, for example, 90 to 100 percent of the pure compound may be used.

C. Diepoxide Component

The second essential reactant in the condensation process, the diepoxide, is a compound having two vicinal epoxide groups (oxirane rings) in terminal (or optionally non-terminal) positions in the molecule, usually in the form of an oxygen atom bound to two terminal carbons of an alkyl group, though the epoxide may also be on a ring, such as a cyclohexyl ring. Suitable diepoxides are terminal diepoxyalkanes, e.g., 1,2-epoxy-3,4-epoxybutane, 1,2-epoxy-5,6-epoxyhexane, 1,2-epoxy-7,8-epoxyoctane and the like. Others are terminal diepoxides containing ether linkages, such as bis(2,3-epoxypropyl)ether and bis(2,3-epoxy-2-methylpropyl)ether; diglycidyl ethers of alpha, omega glycols such as the diglycidyl ethers of ethylene glycol, trimethylene glycol, and tetramethylene glycol; and diglycidyl ethers of dihydric phenols.

Diglycidyl derivatives of the dihydric phenols and amines referred to above are generally suitable for use in this invention. One may suitably use the diglycidyl derivative of the same phenol or amine which is employed as the other reactant.

In preparing the products of this invention the epoxy reagent may be a pure diepoxide or a crude mixture containing a substantial proportion of diepoxide, e.g., 70% or more. It is important, however, tht the crude reagent is free of monoepoxide and of monohydric alcohol or phenol. The desired polyepoxides used herein have the structures shown below:

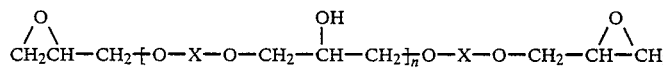

III.

and

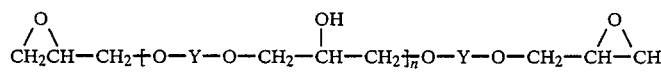

IV.

The number "n" has a value of 0 to about 6, preferably 0 to about 2, more preferably zero.

A preferred diepoxide is the diglycidyl ether of BPA. Such diepoxides are available from Shell Chemical Company as EPON ® Resins 825 and 828. Shell EPON Resin 825 is an essentially pure diepoxide of BPA (where n=0) while EPON Resin 828 is a diepoxide of BPA having a slightly higher average molecular weight and containing a small amount of n=1.

D. Selection of Stiff Units and Flexible Units for Stiff Segments and Flexible Segments A key aspect of the present invention is the selection and location of the stiff units (SU and SU') and flexible units (FU and FU') for the stiff segments (X) and flexible segments (Y). As discussed above, the stiff segment (X) may be located in the amine component, the diphenoxy component or diepoxide component or in all components. For ease of synthesis it is preferred that the stiff segment be in either the diepoxide component or the amine component. The selection will depend upon the particular components to be employed. For example, since the diepoxide of BPA is readily available, it may be preferable to use such a resin in the synthesis. Since the diepoxide of BPA has one flexible unit and two stiff units, it has an $$\frac{SU'}{FU'} \text{ of } \frac{2}{1}$$

or 2 and will therefore be the flexible segment Y. Then one must use an amine component having sufficient number of stiff units (SU) and flexible units (FU) to obtain the desired ratios and polymer characteristics.

More particulars on these ranges and selections are found in the discussion of the Structures of the Resulting Polymers.

E. Catalyst and Reaction Conditions

The condensation reaction between the amine component and the diepoxide component does not normally require a catalyst. In admixture with phenols, however, the presence of a condensation catalyst, typically a basic condensation catalyst is required. The catalyst may, for example, be added as a concentrated aqueous solution of sodium or potassium hydroxide or a sodium or potassium salt of a phenol. One may also use halides, carboxylates or other nucleophiles. It is sometimes desirable to use as catalyst a sodium salt of the same phenol which is used as a reactant or crosslinker. These salts are generally solids which are dissolved in the reaction mixture. It has been found that very satisfactory results are also obtained when using concentrated aqueous sodium hydroxide or benzyltrimethyl ammonium hydroxide. When the catalyst is added as an aqueous solution, a concentrated solution is used since it is not desirable to have more than a small amount of water present in the reaction mixture. The useful range of catalyst concentration is from 0.0001 to 0.100 mole per mole of the contained amine plus phenol. For best results the concentration is preferably between 0.001 and 0.010 mole per mole.

It is preferred to keep the water content of the reaction mixture as low as possible, preferably below 0.5% by weight, more preferably below 0.2% by weight, and still more preferably below 0.12% by weight. In any event, the water content is to be maintained so as not to exceed about 1 percent by weight.

Careful control of the ratio of amine and diglycidyl ether in the reaction mixture is of importance in order to obtain a product having the desired characteristics. When technical grades of one or several reagents are employed, the correct ratio is maintained by determining the epoxy equivalence and the amine hydrogen equivalency of the reagents and carrying out the reaction with a mixture which contains not less than 0.8 amine hydrogen groups per epoxide group and not more than 1.2 amine hydrogen groups per vic epoxide group

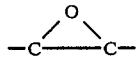

Best results are obtained with amine hydrogen/epoxy ratios in the range from 0.96 to 1.04. When a phenolic reagent is additionally employed in the process then the phenol present is considered part of the amine reagent for purposes of calculating the proper ratio of reactants.

The reaction is typically carried out in solution in a solvent which meets the following criteria: (1) It is capable of maintaining reactants and reaction products in solution, at reaction temperatures, in the concentrations employed. These concentrations generally range between 20 and 60 percent by weight of the total reaction mixture. When the original concentration is high, it is generally necessary to add additional solvent during the course of the reaction to reduce the viscosity of the mixture and to maintain the product in solution. (2) It does not react significantly with epoxide groups or amine groups. Water and alcohols, for example, tend to interract with the reactants and are therefore not suitable as solvents. (3) It is readily and completely removable from the final reaction mixture to permit recovery of a resin substantially completely free of solvent. In the production of resin for use in molding, extrusion, and the like, solvent is removed from the reaction mixture. In the production of resin for surface coatings, the resin may remain associated with solvent until it is actually applied as a coating and the solvent is removed by evaporation under sitable conditions. (4) Its boiling point must be such that the reaction can be carried out at 75° to 150° C. at a practical pressure. The solvent may be a mixture of individual compounds.

Useful solvents which meet those criteria are, for example, certain ketones and ethers. Methyl ethyl ketone is a preferred solvent. Cyclohexanone, methyl isobutyl ketone and the other ketones may be used. Ethers, such as dioxane, tetrahydrofuran, dimethoxyethane and lower alkyl (methyl or ethyl) ethers of ethylene glycol are suitable, alone or in admixture with ketones. Other solvents whichmeet the above criteria may be employed if desired, such as N-methyl pyrrolidone.

While in the examples which follow the synthesis was performed in solution, it is also possible (and desirable in some cases) to do the synthesis in the absence of solvent, i.e. as a melt. In such cases it may be desirable to use the diepoxide containing the stiff segment since the melting point of the mixture is minimized.

II. RESULTING POLYMERS

A. Structures

As mentioned above, a key aspect of the present invention is the selection and location of the stiff units (SU and SU') and the flexible units (FU and FU!) for the stiff segments (X) and flexible segments (Y). Great latitude is provided for the selection and location of the particular components. For the most part the properties and performance of the resulting polymers depend primarily on the relative number of stiff units and flexible units (each such unit being assigned a value of one). However, there are certain important ratios and values that need to be followed.

Note that it is not necessary that the segments contain flexible units. For example, DGBPFL does not contain flexible units and is perfectly satisfactory.

The first important ratio is the average number of total stiff units divided by the average number of total flexible units. This ratio is defined by the relationship:

$$\frac{\frac{a}{a+b} \cdot SU + \frac{b}{a+b} \cdot SU'}{\frac{a}{a+b} \cdot FU + \frac{b}{a+b} \cdot FU'}.$$

Preferably this ratio is greater than 4 and less than about 20 for high temperature applications (e.g. aerospace). More preferably this ratio is greater than 5 and less than 10. This ratio is important because it is an important factor in determining the Tg, or heat resistance of the polymer. Ratios lower than 4 (e.g. 2) and higher than 20 are also contemplated herein.

The second important ratio is that SU/FU must be equal to or greater than SU'/FU', preferably greater. In other words, the stiff segment (X) must have an equal or higher ratio of SU/FU than the flexible segment (Y) ratio of SU'/FU'. This is important bevcause it helps determine the Tg/toughness balance. Preferably SU/FU>SU'/FU'+0.5. In a preferred embodiment SU'/FU' is between 1 and 4, preferably between 2 and 3. For example, where it is preferred to use the diglycidyl ether of BPA, the SU'/FU' ratio is 2/1 or 2.

The third important ratio is the relative amounts of stiff segments and flexible segments, i.e. a/a+b. In the broadest case the ratio of a/a+b is less than or equal to 1. The preferred ratios of a/a+b are between about 0.2 and 0.8, more preferably between about 0.3 and 0.7, most preferably between about 0.4 and 0.6.

B. Light Crosslinking

Another important aspect of the present invention relates to the light crosslinking of the polymer molecules to form the resulting polymer matrix. The concept and process for light crosslinking of such polymers is another novel and unobvious aspect of the present invention. In the broadest sense, light crosslinking refers to the crosslinking of between 1 and 50 out of each 100 repeat units to repeat units of other molecules. Preferably, the crosslinking density is between 2 and 40 out of 100, more preferably between about 5 and 25 repeat units per 100 repeat units. "Light crosslinking" is distinguished from the normal crosslinking or curing of epoxy resins where the crosslink density approaches 100 (stoichiometric) molecules or repeat units per 100 molecules or repeat units.

There are basically three different techniques that may be used to obtain lightly crosslinked matrices. One technique involves the use of a slightly greater number of diepoxide groups than amine groups (see earlier section on I.E. Catalyst and Reaction Conditions). When using this technique the repeat units will crosslink through the reaction of the secondary hydroxyl groups with the remaining epoxide groups. Once the thermoplastic polymer is prepared, it may be used alone or with a reinforcing fiber in an FRC-type (fiber reinforced composite) composition, wherein the polymer mass is heated to an elevated temperature (e.g. above 170° C.) and held at that temperature for the necessary time (typically about 2 to about 24 hours) to obtain crosslinking.

Another technique to obtain light crosslinking is to incorporate an appropriate amount of tri- or higher functional epoxide or tri- or higher functional phenol or amine in the preparation of the polymer. The crosslinking agent, when added as a separate component, replaces a portion of the amine component or the epoxide component, as desired. For example, if 20% crosslinking agent is used, then 20% of the amine component is replaced on an equivalent basis.

Examples of suitable multifunctional epoxide polymers include Epon® Resin 1031 and Epon® Resin DPS-164. Epon Resin DPS-164 has the general formula

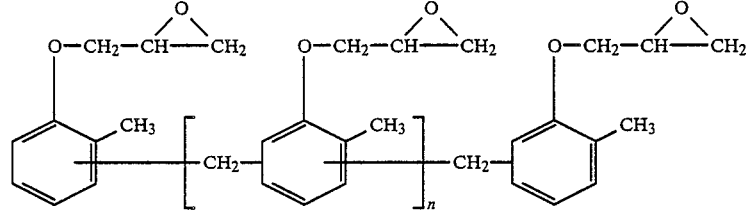

where n equals an average of 3.

Epon Resin 1031 has the structure

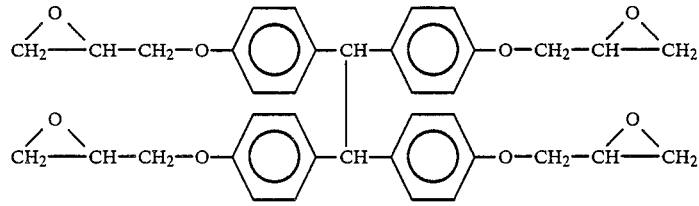

Other crosslinking agents include multifunctional amines such as EPON HPT ™ Curing Agents 1061 and 1062, having the molecular structure:

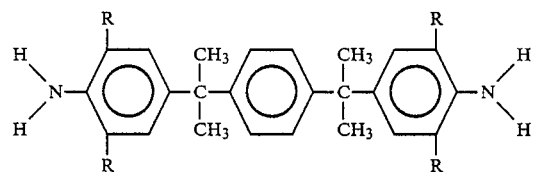

where R is H for CA 1061 and R is CH$_3$ for CA 1062.

Still other crosslinking agents include

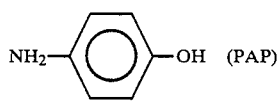

and

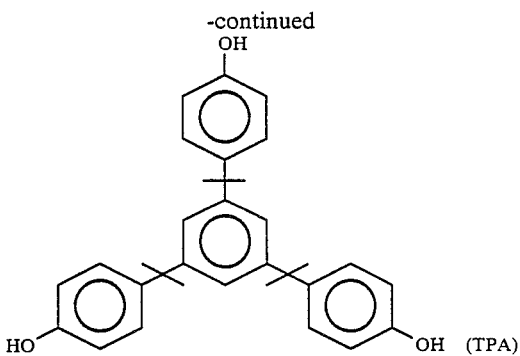

A third technique to obtain light crosslinking involves the addition of crosslinking agents, such as triepoxides, etc., to the resulting polymer. This technique is not preferred since it is more difficult to incorporate the crosslinking agent in the polymer after synthesis than before synthesis.

The amount of crosslinking agent chosen is selected to achieve the desired level of light crosslinking, as opposed to the normal crosslinking used for epoxy resins. Accordingly, when using a crosslinking agent such as EPON Resin 1031, the amount of equivalents used is 2 to 20%. Likewise, when the crosslinking agent is EPON HPT Curing Agent 1061, the amount of equivalents used is 5-50%. Further, the stiff units and flexible units in said crosslinking agent should also be included in determining the various ratios, etc., in the polymer composition.

C. Formulations and Composites

The composition optionally, but preferably for high-performance applications such as automotive and aerospace, contains a reinforcing substrate. Suitable reinforcing materials include, for example, glass fibers, carbon fibers, Kevlar, boron, calcium carbonate, talc, alumina, asbestos and the like. The preferred fibrous reinforcing material for high-performance applications is selected from the group consisting of glass fibers, carbon fibers, boron fibers and Kevlar fibers, with continuous carbon fiber being most preferred. The fibrous reinforcing material will be present in the composition in an amount effective to impart increased strength to the cured composition, generally from about 40 to about 95 weight percent, usually from about 60 to about 80 weight percent, based on the weight of the total composition.

The present composition can be applied to the fibrous reinforcing material from the melt or solution by methods known in the art. Among the various processes useful with the present invention include resin transfer molding (RTM), pultrusion, filament winding and the use of prepregs. Such methods are known in the art, and are disclosed, for example, in the Handbook of Composites, Lubin, Ed., Van Nostrand Reinhold Company, 1982, pages 321–532, and in the book by Delmonte titled Technology of Carbon and Graphite Fiber Composites, Delmonte, Van Nostrand Reinhold Company, 1981.

One method of current preferred interest involves the use of prepregs. In that system, the polymer composition/curing agent-impregnated substrate, or "prepreg", or a laminate prepared from a plurality of prepregs, is then cured. When the system is based on $\alpha,\alpha'$-bis[1-(2,3-epoxypropoxy)-2-napthyl]-para-diisopropylbenzene and N,N'-dimethyl-$\alpha,\alpha'$-bis(4-aminophenyl)-p-diisopropylbenzene, the curing is typically accomplished at a temperature of about 150° to about 200° C. for about 1 to 24 hours under vacuum or under a presence of 1 atmosphere to 150 psi, to form the structural composite article.

D. Uses

The compositions of the present invention have particular application in the aerospace industry where the high performance obtainable with the present invention is required. In particular, RIM may be used to prepare large parts, such as helicopter blades. Pre-pregs may be used to prepare parts such as wings and the like. Filament winding may be used to prepare an entire fuselage, while pultrusion may be used to prepare parts having a constant cross section.

The invention composition can optionally include additives for control or modification of various properties of the composition in its cured or uncured state, including cure rate accelerators or retardants, tackifiers and the like.

To illustrate the present invention, the following illustrative embodiments and comparative examples are given. It is to be understood, however, that the embodiments and examples are given for the purpose of illustration only and the invention is not to be regarded as limited to any of the specific materials or conditions used in the specific embodiments.

As used in the following examples, Epoxy Resin A is a liquid glycidyl polyether of 2,2-bis(4-hydroxyphenyl)-propane having an epoxide equivalent weight of 170-174 and an average molcular weight of about 345.

Epoxy Resin B is a liquid glycidyl polyether of 2,2-bis(4-hydroxyphenyl)propane having an epoxide equivalent weight of 180-195 and an average molecular weight of about 380.

The compositions were tested according to the following test procedures:

Flexural properties of neat resins were evaluated according to ASTM D790 method using ⅛ in. thick specimens. Specimens were tested both in Dry (at Room Temperature and ~75% R.H.) and Hot/Wet (after immersion in boiling water for 48 hours, test at 200° F., 5 min. equilibration time) conditions.

Fracture toughness, $K_q$, was measured using mini-compact tension specimens (see W. B. Jones, et al Am. Chem. Soc., Div. Polym. Chem., Polym. Prepr., 22, 1981). All specimens were slotted to a Chevron shape and then precracked with a razor blade.

Tensile properties were measured according to ASTM D638 method.

Swelling in solvents was evaluated by measuring weight gain per unit of initial weight after immersion in solvent for a specified time at room temperature.

ILLUSTRATIVE EMBODIMENT I

In Illustrative Embodiment I, two of the components used in making the polymers of the present invention are prepared.

Synethesis of $\alpha,\alpha'$-bis(1-hydroxy-2-napthyl)-para-diisopropylbenzene (BNDB)

The synthesis of BNDB was accomplished using 1-napthol, p-Diol ($\alpha,\alpha'$-dihydroxy-para-diisopropylbenzene), 1,1,2-trichloroethane, and concentrated hydrochloric acid in a molar ratio of 8:1:4:1.02. Thus, a mixture of 1-napthol, p-Diol, and 1,1,2-trichloroethane was heated as a slurry (which dissolves) to 65°–70° C. with agitation under nitrogen. Conc. HCl was added slowly, controlling the temperature of the reaction to below 82° C. The reaction was allowed to proceed for 50 minutes after the addition of the HCl at 70°–80° C. BNDB (M.W. 446) precipitated out of reaction in 90+% yield. The BNDB melts at 245°–255° C.

Synthesis of $\alpha,\alpha'$-bis[1-(2,3-epoxypropoxy)-2-napthyl]-para-diisopropylbenzene (DGBNDB)

The synthesis of DGBNDB was accomplished using BNDB, epichlorohydrin (ECH), isopropanol (IPA), and water in a molar ratio of 1:15:13.5:13 and staging the addition of 20% wt. Sodium Hydroxide in water. To a slurry of BNDB in ECH, IPA and water at 70° C. under nitrogen was added slowly 1 mole of NaOH as 20% wt. NaOH in water per 1 mole of BNDB and reacted until the reaction mass was a solution. The brine was separated from the organic layer and discarded. This process of slow NaOH addition and brine removal was repeated three times more at 0.8, 0.8, and 0.4 moles of NaOH per mole of BNDB. After the last brine removal the organic phase was water washed and then vacuum-evaporated until neat, molten resin was obtained. The resin was dissolved 20% wt. in methylisobutyl ketone (MIBK) and then heated to 90° C. under nitrogen. A solution of 5% wt. NaOH in water equal to 25% wt. of the total reaction mass was charged to the resin solution and the heterogeneous mass allowed to react at 90°–95° C. for two hours. The brine was removed and the MIBK solution was washed with water until the wash water was the same pH as it started. The MIBK was distilled at atmospheric pressure until the resin started to precipitate. The hot MIBK slurry was cooled to room temp. with stirring and the resin collected on a filter and dried in a vacuum oven at 100° C. overnight. The resin melts at 160° C. (approx.) and chromatographs as essentially 1 peak of 96%+ area by reverse phase HPLC. The WPE is 280-284 (theory is 279) and the Sap. Cl is <0.01%wt.

N,N'-Dimethyl-$\alpha,\alpha'$-bis(4-aminophenyl)-p-diisopropylbenzene (NMADB)

N-methylaniline (8 mol), p-Diol ($\alpha,\alpha'$-dihydroxy-p-diisopropylbenzene) (1 mol), and Super Filtrol #1 catalyst (4% wt) were heated in a reactor equipped with a Dean-Stark Trap and Nitrogen to a reaction temperature temperature of 180° C. (removing the N-methylaniline/water azeotrope of p-Diol dehydration) and held at that temperature for 1 hour. The reaction mass was then cooled to a comfortable temperature and the Super Filtrol was removed by filtering through a Buchner funnel with Celite filter-aid. N-methylaniline was removed by vacuum distillation and the crude product was poured with stirring into methanol (approximately 1:1 MeOH/prdct.) and allowed to cool. The product crystallized out in 95+% purity by amine N titration and HPLC. The melting point was 115°–122° C.

ILLUSTRATIVE EMBODIMENT II

An Illustrative Embodiment II, a polymer according to the present invention was made starting with DGBNDB and NMADB (prepared as in Illustrative Embodiment I), and EPON HPT™ CA 1061 curing agent (described earlier).

All of the materials used were recrystallized and thoroughly dried in a vacuum oven at 1 mm Hg vacuum before they were used. Component specifications were as follows:

| | |
|---|---|
| DGBNDB | WPE = 282–284 (theo. 279); Sap. Cl < .01% wt. |
| NMADB | Amine N = 5.312 meq./gm (theo. 5.376 meq./gm); M.P. = 115–122° C. |
| Epoxy HPT CA 1061 | M.P. = 160–161° C. |

Calculations and Stoichiometry:

Theoretical Amine Hydrogen equivalent values were used in calculating charges for NMADB (0.74 eq) and HPT CA 1061 (0.26 eq). Actual WPE was used in calculating the charge for DGBNDB (1 eq).

Procedure:

The polymer was made by melting the three components together at 190° C. in a vacuum erlenmyer flask, degassing at 1 mm Hg until bubling ceased, pouring the molten pre-polymer into a mold (made of two glass plates treated with a releasing agent, preheated in a forced draft oven at 190° C.) and curing the polymer for 24 hours. At the end of the curre cycle, the polymer-in-mold was taken out of the oven and allowed to cool below its Tg and then the plates were popped loose. The following properties were obtained:

Tg = 168° C.

$K_q = 2300$ psi $\sqrt{in}$

Flex modulus = 525 KSI

Flex Strength = 15.8 KSI

Flex Elongation = 3.0%

Gel Content = 90%

ILLUSTRATIVE EMBODIMENT III

In Illustrative Embodiment III various polymers were prepared in a manner similar to that described in Illustrative Embodiment II.

The various materials utlized herein are described below in the Structure Legend:

| Type | Symbol | Chemical Name |
|---|---|---|
| Phenols | | |
| | BP | 4,4'-dihydroxybiphenyl |
| | BPA | 2,2-bis(4-hydroxyphenyl)propane |
| | BPC | 4,4'-dihydroxybenzophenone |
| | HFBPA | 1,1,1,3,3 3-hexafluoro-2,2-bis(4-hydroxyphenyl)propane |
| | BPFL | 9,9-bis(4-hydroxyphenyl)fluorene |
| | BPAQ | 9,9-bis(4-hydroxyphenyl)-10-anthrone |
| Epoxides | | |
| | DGBPA | 2,2-bis[4-(2,3-epoxypropoxy)phenyl]propane |
| | DGBPFL | 9,9-bis[4-(2,3-epoxypropoxy)phenyl]fluorene |
| | DGBP | 4,4'-bis(2,3-epoxypropoxy)biphenyl |
| | DGBPAQ | 9,9-bis[4-(2-3-epoxypropxy)phenyl]-10-anthrone |
| | DGBNDB | α,α'-bis[1-(2,3-epoxypropoxy)-2-napthyl]-para-diisopropylbenzene |
| Amines | | |
| | ADA | Aminoadamantane |
| | ACPH | N—(4-amino-2-methylphenyl)-4-chlorophthalimide |
| | NAPH | N—aminophthalimide |
| | AAP | 4-aminoacetophenone |
| | DMA | 2,6-dimethylaniline |
| | DEA | 2,6-diethylaniline |
| | DIPA | 2,6-disipropylaniline |
| | NMADB | N,N'—dimethyl-α,α'-bis(4-aminophenyl)-p-diisopropylbenzene |
| | NEADB | N,N'—diethyl-α,α'-bis(4-aminophenyl)-p-diisopropylbenzene |
| | ADB | α,α'-bis(4-aminophenyl)-p-diisipropylbenzene |
| | NBMDA | N,N'—di-sec-butylbis(4-aminophenyl)methane |
| | BNDB | α,α'-bis(1-hydroxy-2-napthyl)-para-diisopropylbenzene |
| Crosslinking Agents | | |
| | DEADB | αα'-bis(3,5-diethyl-4-hydroxyphenyl)-p-diisopropylbenzene |

-continued

STRUCTURE LEGEND

| Type | Symbol | Chemical Name |
|---|---|---|
| | DMADB | Epon Curing Agent HTT 1062 |
| | ADB | Epon Curing Agent HPT 1061 |
| | EOCN | Epon Resin DPS-164 |
| | TGTPE | Epon Resin 1031 |
| | DDS | Diaminodiphenyl sulfone |
| | TPA | α,α',α''-tris(4-hydroxyphenyl)-1,3,5-triisopropylbenzene |

The preparation details of the polymers are described in Table 1 and the properties are described in Table 2. Referring to Table 1, the basic formulation involves an amine (A), a diepoxide (E), and a crosslinking agent (X). The amount of crosslinking agent used is based on needed stoichiometric equivalents and is designated as "%x". In some cases a fraction of the amine is substituted with a different amine or with a diphenol. These components—Y and Z—are designated along with the percent employed—% Y, % Z. Also designated in Table 1 is the amine to epoxide ratio (A/E), which would also include anything substituted for amine. In addition, the % catalyst is noted where a catalyst is used. Since catalysts are not required for the typical amine/epoxy polymer, catalysts were used in only a few of the examples. When used, the catalyst was monosodium BPA or monosodium BPFL.

The cure schedule is also shown, T/t. "T" refers to temperature of cure and "t" refers to the hours at that temperature. The various cure schemes are as follows:

T/t  A = 190° C./24 hr  
B = 210° C./24 hr  
C = 110° C./16 hr + 150° C./24 hr  
D = 130° C./72 hr + 180° C./2 hr  
E = 150° C./16 hr + 180° C./4 hr  
F = 150° C./16 hr + 200° C./6 hr

The property data for the various polymers are presented in Table 2. For most of the polymers, Tg and $K_q$ are given. For some polymers solvent resistance is shown as percent weight gain when immersed in particular materials—MEK is methylethylketone, MC is $CH_2Cl_2$ and $H_2O$ is water. The polymers were checked at room temperature (RT) after reaching equilibrium (Eq). Flex data is given for both dry and hot/wet (h/w) conditions. Gel is reported in some cases. Where the value given for gel is "0", that means that the polymer is thermoplastic and has *not* been cured to a thermoset. Gel was not measured in all cases.

TABLE 1

| Run # | A | E | X | % X | Y | % Y | Z | % Z | A/E | Cat % | T/t |
|---|---|---|---|---|---|---|---|---|---|---|---|
| 1 | AAP | DGBPFL | DMADB | 10 | | | | | 1.00 | 0 | F |
| 2 | AAP | DGBPFL | | | NMADB | 10 | | | 1.00 | 0 | F |
| 3 | ACPH | DGBPA | DMADB | 10 | | | | | 1.00 | 0 | A |
| 4 | NAPH | DGBPA | DMADB | 10 | | | | | 1.00 | 0 | A |
| 5 | ADA | DGBPA | ADB | 10 | | | | | 1.00 | 0 | A |
| 6 | ADA | DGBPA | ADB | 0 | | | | | 0.96 | 0 | E |
| 7 | ADA | DGBPA | ADB | 20 | | | | | 1.00 | 0 | A |
| 8 | NBMDA | DGBPFL | ADB | 10 | DEA | 15 | | | 0.96 | 0 | F |
| 9 | NBMDA | DGBPFL | ADB | 10 | DEA | 40 | | | 0.96 | 0 | F |
| 10 | NBMDA | DGBPFL | ADB | 10 | DEA | 65 | | | 0.96 | 0 | F |
| 11 | NBMDA | DGBPFL | DDS | 10 | DEA | 65 | | | 0.96 | 0 | F |
| 12 | NBMDA | DGBPFL | DDS | 20 | DEA | 55 | | | 0.96 | 0 | F |
| 13 | NBMDA | DGBPFL | DDS | 30 | DEA | 45 | | | 0.96 | 0 | F |
| 14 | NBMDA | DGBPFL | DDS | 10 | DEA | 40 | | | 0.96 | 0 | F |
| 15 | NBMDA | DGBPFL | DDS | 20 | DEA | 30 | | | 0.96 | 0 | F |
| 16 | NBMDA | DGBPFL | DDS | 30 | DEA | 20 | | | 0.96 | 0 | F |
| 17 | DEA | DGBPFL | ADB | 10 | | | | | 1.00 | 0 | E |
| 18 | DEA | DGBPFL | DMADB | 10 | | | | | 1.00 | 0 | F |
| 19 | DEA | DGBPFL | DMADB | 10 | | | | | 1.00 | 0 | E |
| 20 | DEA | DGBPFL | DMADB | 10 | | | | | 1.00 | 100 | E |
| 21 | DEA | DGBPFL | DMADB | 10 | | | | | 1.00 | 0 | D |
| 22 | DEA | DGBPFL | DMADB | 20 | | | | | 1.00 | 0 | F |
| 23 | DEA | DGBPFL | DMADB | 10 | | | | | 1.06 | 0 | F |
| 24 | DEA | DGBPFL | TPA | 10 | | | | | 0.96 | 100 | F |
| 25 | DEA | DGBPFL | TPA | 20 | | | | | 0.96 | 100 | F |
| 26 | DEA | DGBPFL | TPA | 5 | | | | | 1.00 | 100 | F |
| 27 | DEA | DGBPFL | TPA | 10 | | | | | 1.00 | 0 | F |
| 28 | DEA | DGBPFL | TPA | 20 | | | | | 1.00 | 100 | F |
| 29 | DEA | DGBPFL | | | NMADB | 50 | | | 0.96 | 100 | F |
| 30 | DEA | DGBPFL | | | NMADB | 75 | | | 0.96 | 100 | F |
| 31 | DEA | DGBPFL | | | BPA | 25 | | | 0.96 | 50 | F |
| 32 | DEA | DGBPFL | | | BPA | 25 | | | 0.96 | 100 | F |
| 33 | DEA | DGBPFL | | | BPA | 50 | | | 0.96 | 50 | F |
| 34 | DEA | DGBPFL | | | BPA | 50 | | | 0.96 | 100 | F |
| 35 | DEA | DGBPFL | | | BPA | 75 | | | 0.96 | 100 | F |
| 36 | DEA | DGBPFL | | | BPA | 75 | | | 0.96 | 50 | F |
| 37 | DIA | DGBPFL | DMADB | 10 | NMADB | 15 | NBMDA | 35 | 1.04 | 0 | F |
| 38 | DMA | DGBPA | DMADB | 0 | | | | | 1.00 | 0 | C |
| 40 | DMA | DGBPA | DMADB | 10 | | | | | 1.00 | 0 | C |
| 41 | DMA | DGBPA | DMADB | 15 | | | | | 1.00 | 0 | C |
| 42 | DMA | DGBPA | DMADB | 20 | | | | | 1.00 | 0 | C |

TABLE 1-continued

| | COMPONENTS | | | | | | | | | Cat | |
|---|---|---|---|---|---|---|---|---|---|---|---|
| Run # | A | E | X | % X | Y | % Y | Z | % Z | A/E | % | T/t |
| 43 | DMA | DGBPA | DMADB | 30 | | | | | 1.00 | 0 | C |
| 44 | DMA | DGBPA | DMADB | 40 | | | | | 1.00 | 0 | C |
| 45 | DMA | DGBPAQ | DMADB | 15 | NMADB | 10 | NBMDA | 35 | 1.04 | 0 | F |
| 46 | DMA | DGBPAQ | DMADB | 15 | NMADB | 10 | NBMDA | 25 | 1.04 | 0 | F |
| 47 | DMA | DGBPFL | ADB | 15 | | | | | 1.00 | 0 | E |
| 48 | DMA | DGBPFL | DEADB | 15 | | | | | 1.00 | 0 | E |
| 49 | DMA | DGBPFL | DMADB | 10 | NMADB | 15 | NBMDA | 35 | 1.04 | 0 | F |
| 54 | DMA | DGBPFL | DMADB | 15 | NMADB | 10 | NBMDA | 35 | 1.04 | 0 | F |
| 55 | DMA | DGBPFL | DMADB | 25 | NMADB | 0 | NBMDA | 35 | 1.04 | 0 | F |
| 61 | DMA | DGBPFL | DMADB | 15 | NMADB | 10 | NBMDA | 25 | 0.96 | 0 | F |
| 62 | DMA | DGBPFL | DMADB | 15 | NMADB | 10 | NBMDA | 25 | 1.00 | 0 | F |
| 63 | DMA | DGBPFL | DMADB | 15 | NMADB | 10 | NBMDA | 25 | 1.04 | 0 | F |
| 64 | DMA | DGBPFL | DMADB | 15 | NMADB | 10 | NBMDA | 25 | 1.06 | 0 | F |
| 65 | DMA | DGBPFL | DMADB | 15 | NMADB | 10 | NBMDA | 25 | 1.08 | 0 | F |
| 66 | DMA | DGBPFL | DMADB | 15 | NMADB | 10 | NBMDA | 30 | 1.04 | 0 | F |
| 73 | DMA | DGBPFL | DMADB | 15 | | | | | 0.96 | 0 | F |
| 74 | DMA | DGBPFL | DMADB | 20 | | | | | 1.00 | 0 | E |
| 75 | DMA | DGBPFL | DMADB | 15 | | | | | 1.04 | 0 | F |
| 76 | DMA | DGBPFL | DMADB | 15 | | | | | 1.08 | 0 | F |
| 77 | DMA | DGBPFL | DMADB | 15 | | | | | 1.10 | 0 | F |
| 78 | DMA | DGBPFL | PAP | 15 | | | | | 1.00 | 100 | F |
| 79 | NMADB | DGBNDB | ADB | 0 | | | | | 1.00 | 0 | A |
| 80 | NMADB | DGBNDB | ADB | 13 | | | | | 1.00 | 0 | A |
| 81 | NMADB | DGBNDB | ADB | 20 | | | | | 1.00 | 0 | A |
| 82 | NMADB | DGBNDB | ADB | 26 | | | | | 1.00 | 0 | A |
| 83 | NMADB | DGBNDB | ADB | 36 | | | | | 1.00 | 0 | A |
| 84 | NMADB | DGBNDB | ADB | 50 | | | | | 1.00 | 0 | B |
| 85 | NMADB | DGBNDB | ADB | 75 | | | | | 1.00 | 0 | B |
| 86 | NMADB | DGBNDB | ADB | 100 | | | | | 1.00 | 0 | B |
| 87 | NMADB | DGBPFL | ADB | 0 | | | | | 1.00 | 0 | A |
| 88 | NMADB | DGBPFL | ADB | 100 | | | | | 1.00 | 0 | B |
| 89 | NMADB | DGBPFL | ADB | 50 | | | | | 1.00 | 0 | B |

TABLE 2

| Run # | Tg °C. | $K_q$ PSI $\sqrt{in}$ | % Wt Gain (RT, Eq) | | | Flex Data (KSI) | | | | Gel % |
|---|---|---|---|---|---|---|---|---|---|---|
| | | | MEK | MC | $H_2O$ | E, dry | E, h/w | Stress | Strain, % | |
| 1 | 183 | 620 | | | | 570 | 430 | 18.6 | 3.5 | |
| 2 | 171 | | | | | | | | | 80 |
| 3 | 167 | | | | | | | | | 96 |
| 4 | 132 | | | | | | | | | 90 |
| 5 | 142 | 820 | | | 1.8 | 439 | 402 | 19.5 | 9 | 96 |
| 6 | 123 | | | | | | | | | 0 |
| 7 | 151 | 740 | | | 1.8 | 431 | 395 | 19.8 | 9 | 98 |
| 8 | 143 | 1200 | | | 1.1 | 432 | 360 | 19.8 | 9 | 92 |
| 9 | 150 | 1100 | | | 1.4 | 434 | 371 | 20.2 | 7 | 92 |
| 10 | 158 | 750 | | | 1.4 | 440 | 387 | 20.8 | 9 | 93 |
| 11 | 155 | | | | | | | | | 75 |
| 12 | 161 | | | | | | | | | 90 |
| 13 | 173 | | | | | | | | | 95 |
| 14 | 150 | | | | | | | | | 76 |
| 15 | 157 | | | | | | | | | 89 |
| 16 | 163 | | | | | | | | | 92 |
| 17 | 160 | | | | | | | | | 85 |
| 18 | 158 | | | | | | | | | 85 |
| 19 | 158 | | | | | | | | | 85 |
| 20 | 162 | | | | | | | | | 91 |
| 21 | 165 | 1000 | | | | 477 | | 15 | 3 | 80 |
| 22 | 164 | | | | | | | | | 93 |
| 23 | 157 | | | | | | | | | 74 |
| 24 | 158 | | | | | | | | | 95 |
| 25 | 162 | | | | | | | | | 97 |
| 26 | 156 | | | | | | | | | 88 |
| 27 | 155 | | | | | | | | | 92 |
| 28 | 160 | | | | | | | | | 94 |
| 29 | 163 | | | | | | | | | 73 |
| 30 | 161 | | | | | | | | | 0 |
| 31 | 161 | 800 | | | 1.7 | 439 | 391 | 17.1 | 5 | 51 |
| 32 | 163 | | | | | | | | | 93 |
| 33 | 166 | 900 | | | 1.9 | 427 | 387 | 12.5 | 3 | |
| 34 | 171 | | | | | | | | | 80 |
| 35 | 173 | | | | | | | | | 88 |
| 36 | 170 | 1450 | | | 2 | 419 | 377 | 9.3 | 2 | |
| 37 | 160 | | | | | | | | | |
| 38 | 110 | 2200 | | | | 425 | | 16.8 | >8 | 0 |
| 40 | 125 | 2500 | 77 | 207 | | 405 | | 17.1 | >8 | 86 |
| 41 | 130 | 2550 | 88 | 229 | 1.9 | 410 | 300 | 17.3 | >8 | 85 |
| 42 | 128 | 2500 | 63 | 167 | | 420 | 270 | 18.5 | >8 | 91 |

TABLE 2-continued

| Run # | Tg °C. | $K_q$ PSI $\sqrt{in}$ | % Wt Gain (RT, Eq) MEK | MC | $H_2O$ | Flex Data (KSI) E, dry | E, h/w | Stress | Strain, % | Gel % |
|---|---|---|---|---|---|---|---|---|---|---|
| 43 | 139 | 1600 | | | | 430 | | 18.3 | >8 | 99 |
| 44 | 143 | 1440 | | | | 435 | | 18.6 | >8 | 97 |
| 45 | 168 | | | | | | | | | |
| 46 | 178 | | | | | | | | | |
| 47 | 174 | | | | | | | | | |
| 48 | 174 | | | | | | | | | |
| 49 | 156 | | | | | | | | | |
| 54 | 161 | | | | | | | | | |
| 55 | 171 | | | | | | | | | |
| 61 | 168 | | | | | | | | | 91 |
| 62 | 170 | | | | | | | | | 98 |
| 63 | 175 | | | | | | | | | 99 |
| 64 | 164 | | | | | | | | | |
| 65 | 159 | | | | | | | | | |
| 66 | 166 | | | | | | | | | |
| 73 | 174 | | | | | | | | | |
| 74 | 178 | | 22 | 157 | 1.7 | | | | | 94 |
| 75 | 188 | | | | | | | | | 92 |
| 76 | 186 | | | | | | | | | |
| 77 | 168 | | | | | | | | | 81 |
| 78 | 176 | | | | | | | | | |
| 79 | 155 | 2300 | | | 1.1 | 512 | 485 | 13.3 | 3 | |
| 80 | 163 | | 116 | 693 | | | | | | 78 |
| 81 | 163 | | 103 | 470 | | | | | | 85 |
| 82 | 168 | 2300 | 87 | 348 | 0.8 | 525 | | 15.8 | 3.0 | 90 |
| 83 | 171 | | | | | | | | | 92 |
| 84 | 177 | 1700 | | | 1 | 540 | 493 | 17.9 | 3.4 | 96 |
| 85 | 190 | 1200 | | | 1 | 544 | 493 | 17 | 3.2 | |
| 86 | 211 | 840 | | | 1.1 | 550 | 499 | 16.8 | 3.1 | |
| 87 | 161 | 1800 | | | 1.3 | 436 | 404 | 20 | 7 | |
| 88 | 246 | 445 | | | 2 | 469 | 367 | 17.8 | 5 | |
| 89 | 198 | 620 | | | 1.6 | 455 | 401 | 22.3 | 9 | |

What is claimed is:

1. A polymer composition comprising lightly crosslinked linear molecules having the repeating structures prior to crosslinking of the general formula:

$$-\!\!\left[A-CH_2-\underset{\underset{OH}{|}}{CH}-CH_2-B-CH_2-\underset{\underset{OH}{|}}{CH}-CH_2\right]\!\!-$$

where A is selected from the group consisting of:

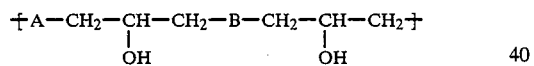

and mixtures thereof, and B is selected from the group consisting of:

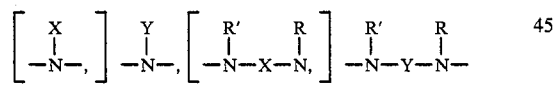

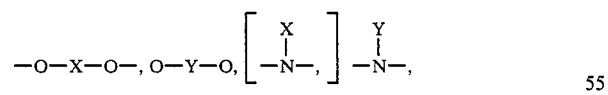

where R and R' are selected from the group consisting of unsubstituted or inertly substituted $C_1$–$C_{20}$ aliphatic, cycloaliphatic or aromatic hydrocarbyl groups, and wherein said repeating structures are lightly crosslinked such that between 1 and 50 of said repeating structures per 100 total repeating structures are crosslinked to repeating structures of other molecules, and where:

(a) "X" represents

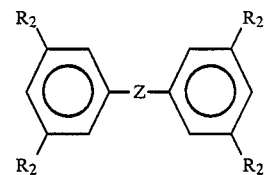

where each $R_2$ is independently selected from H, Cl, Br or $C_1$–$C_5$ alkyl and Z is a gem-bivalent radical having 1 to 2 aromatic hydrocarbon rings and a gem-bivalent non-aromatic ring selected from the group consisting of a ring of 5 carbon atoms, a ring of 6 carbon atoms one of which carbon atoms can bear an oxo oxygen atom and a ring of 5 carbon atoms and one oxygen atom, said gem-bivalent non-aromatic ring being fused to said aromatic rings;

(b) "Y" represents a segment comprising stiff units (SU') and optional flexible units (FU') which stiff units and flexible units are interconnected;

(c) said stiff units, SU and SU', are independently selected from the group consisting of substituted and non-substituted benzene, naphthalene, anthracene and phenanthrene rings, and non-interfering heterocyclic rings;

(d) said flexible units, FU and FU', are independently selected from the group consisting of

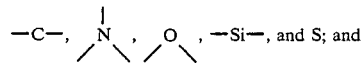

(e) the ratio of the number of stiff units to flexible units in said X segment (SU/FU) is equal to or greater than the ratio of the number of stiff units to flexible units in said Y segment (SU'/FU').

2. The composition of claim 1 wherein A is selected from

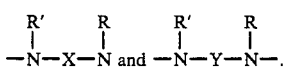

3. The composition of claim 1 wherein the repeating structures are lightly crosslinked such that between 2 and about 40 repeating structures from different molecules per 100 of said repeating structures are crosslinked together.

4. The composition of claim 3 wherein between 5 and 25 per 100 repeating structures are crosslinked together.

5. The composition of claim 1 wherein said linear molecules are prepared by reacting a first component with a second component, said first component being an amine selected from the group consisting of primary monoamines, bis secondary amines and mixtures thereof, and said second component being a diepoxide.

6. The composition of claim 5 wherein said first component is a bis secondary amine and said second component is a diepoxide of a bisphenol.

7. The composition of claim 5 wherein said first component is a primary amine and said second component is a diepoxide of a bisphenol.

8. The composition of claim 5 wherein sid first component and said second component are reacted in the presence of a crosslinking agent.

9. The composition of claim 8 wherein the crosslinking agent is selected from the group consisting of tri- or higher functional epoxides, tri- or higher functional phenolics, tri- or higher functional amines or mixtures thereof.

10. The composition of claim 1 which further comprises a fibrous reinforcing material.

11. The composition of claim 5 which further comprises a fibrous reinforcing material.

12. The composition of claim 10 wherein the fibrous reinforcing material is selected from the group consisting of glass fibers, carbon fibers, boron fibers and Kevlar fibers.

13. The composition of claim 11 wherein the fibrous reinforcing material is selected from the group consisting of glass fibers, carbon fibers, boron fibers and Kevlar fibers.

14. The cured composition of claim 1 having a glass transition temperature of at least about 150° C.

15. A prepreg comprising the composition of claim 1 and a fibrous reinforcing material.

16. A prepreg comprising the composition of claim 13.

17. An article of manufacture prepared from the prepreg of claim 16.

18. The composition of claim 5 also including a third component, said third component being a bisphenol selected from the group consisting of HO-X-OH and HO-Y-OH.

19. The composition of claim 1 having a glass transition temperature below 150° C.

20. The composition of claim 8 wherein said first component is N,N'-dimethyl-α,α'-bis(4-aminophenyl)-p-diisopropylbenzene).

21. The composition of claim 20 wherein said second component is 9,9-bis[4-(2,3-epoxypropoxy)phenyl]fluorene.

22. The composition of claim 21 wherein said crosslinking agent is a multifunctional amine of the formula

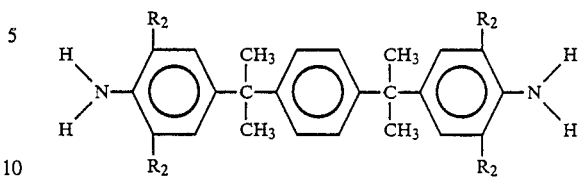

where R₂ is H.

23. The composition according to claim 5 wherein the diepoxide is α,α'-bis[1-(2,3-epoxypropoxy)-2-naphthyl]-para-diisopropylbenzene.

24. The composition according to claim 5 wherein Z is

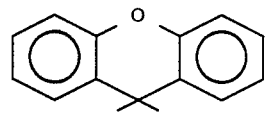

25. The composition according to claim 5 wherein the diepoxide is the diglycidyl ether of 9,9-bis(4-hydroxyphenyl)fluorene.

26. The composition according to claim 5 wherein the average number of total stiff units divided by the average number of total flexible units is greater than 4 and less than 20.

27. The composition according to claim 23 wherein the amine is a bis-secondary amine.

28. The composition according to claim 27 wherein the amine is an aromatic hydrocarbon amine.

29. The composition according to claim 28 wherein the amine is N,N'-dimethyl-α,α'-bis(4-aminophenyl)-p-diisopropylbenzene.

30. The composition according to claim 28 wherein the amine is N,N'-diethyl-α,α'-bis(4-aminophenyl)-p-diisopropylbenzene.

31. The composition according to claim 28 wherein the amine is α,α'-bis(4-aminophenyl)-p-diisopropylbenzene.

32. The composition according to claim 28 wherein the amine is N,N'-di-sec-butylbis(4-aminophenylmethane).

33. The composition according to claim 5 wherein the average number of total stiff units divided by the average number of total flexible units is greater than 5 and less than 10.

34. The composition according to claim 18 wherein a portion of the first component amine is replaced by a bisphenol which is 4,4'-dihydroxybenzophenone.

35. The composition according to claim 18 wherein a portion of the first component amine is replaced by a bisphenol which is 1,1,1,3,3,3-hexafluoro-2,2'-bis(4-hydroxyphenyl)propane.

36. The composition according to claim 18 wherein a portion of the first component amine is replaced by a bisphenol which is 9,9-bis(4-hydroxyphenyl)fluorene.

37. The composition according to claim 18 wherein a portion of the first component amine is replaced by a bisphenol which is 9,9-(4-hydroxyphenyl)-10-anthrone.

38. The composition according to claim 18 wherein a portion of the first component amine is replaced by a bisphenol which is

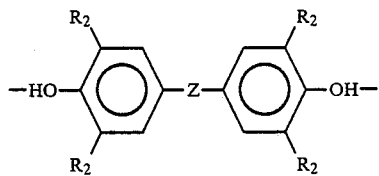

where each R₂ is independently selected from H, Cl, Br or C₁-C₅ alkyl and Z is a substituent having flexible units (FU or FU') and stiff units (SU or SU') where Z is a gem-bivalent radical having 1 to 2 aromatic hydrocarbon rings and gem-bivalent non-aromatic ring selected from the group consisting of a ring of 5 carbon atoms, a ring of 6 carbon atoms one of which carbon atoms can bear an oxo oxygen atom and a ring of 5 carbon atoms and one oxygen atom, said gem-bivalent non-aromatic ring being fused to said aromatic rings.

39. The composition according to claim 38 wherein Z is

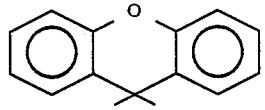

40. The composition of claim 8 wherein said diepoxide is 9,9-bis[4-(2,3-epoxypropoxy)phenyl]fluorene.

41. The composition of claim 40 wherein said first and second components are reacted in the presence of a crosslinking agent which is a multifunctional amine of the formula

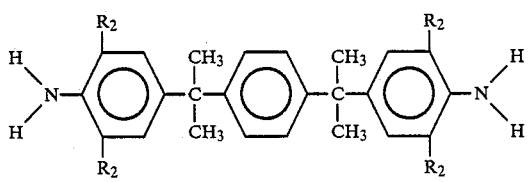

where R₂ is H.

42. A polymer composition comprising lightly crosslinked linear molecules having the repeating structures prior to crosslinking of the general formula:

$$+A-CH_2-CH-CH_2-B-CH_2-CH-CH_2+$$
$$\phantom{+A-CH_2-}OH\phantom{-CH_2-B-CH_2-}OH$$

where A is selected from the group consisting of:

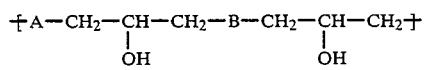

and mixtures thereof, and B is selected from the group consisting of:

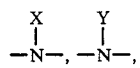

$$\begin{array}{cc} R' & R \\ | & | \\ -N-Y-N- \end{array}$$

where R and R' are selected from the group consisting of unsubstituted or inertly substituted C₁-C₂₀ aliphatic, cycloaliphatic or aromatic hydrocarbyl groups, and wherein said repeating structures are lightly crosslinked such that between 1 and 50 of said repeating structures per 100 total repeating structures are crosslinked to repeating structures of other molecules, and where:

(a) "X" represents a segment comprising stiff units (SU) and optional flexible units (FU), which stiff units and flexible units are interconnected;

(b) "Y" represents a segment comprising stiff units (SU') and optional flexible units (FU') which stiff units and flexible units are interconnected;

(c) said stiff units, SU and SU', are independently selected from the group consisting of substituted and non-substituted benzene, naphthalene, anthracene and phenanthrene rings, and non-interfering heterocyclic rings;

(d) said flexible units, FU and FU', are independently selected from the group consisting of

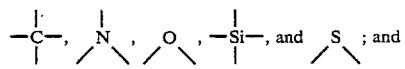

(e) the ratio of the number of stiff units to flexible units in said X segment (SU/FU) is equal to or greater than the ratio of the number of stiff units to flexible units in said Y segment (SU'/FU').

43. A polymer composition comprising lightly crosslinked linear molecules having the repeating structures prior to crosslinking of the general formula:

$$+A-CH_2-CH-CH_2-B-CH_2-CH-CH_2+$$
$$\phantom{+A-CH_2-}OH\phantom{-CH_2-B-CH_2-}OH$$

where A is selected from the group consisting of:

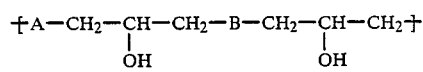

and mixtures thereof, and B is selected from the group consisting of:

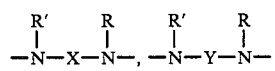

where R and R' are selected from the group consisting of unsubstituted or inertly substituted C₁-C₂₀ aliphatic, cycloaliphatic or aromatic hydrocarbyl groups, and wherein said repeating structures are lightly crosslinked such that between 1 and 50 of said repeating structures per 100 total repeating structures are crosslinked to repeating structures of other molecules, and where:

(a) "X" represents a segment comprising stiff units (SU) and optional flexible units (FU), which stiff units and flexible units are interconnected;

(b) "Y" represents a segment comprising stiff units (SU') and optional flexible units (FU') which stiff units and flexible units are interconnected;

(c) said stiff units, SU and SU', are independently selected from the group consisting of substituted and non-substituted benzene, naphthalene, anthracene and phenanthrene rings, and non-interfering heterocyclic rings;

(d) said flexible units, FU and FU', are independently selected from the group consisting of

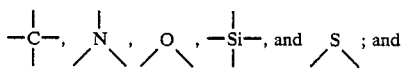

and (e) the ratio of the number of stiff units to flexible units in said X segment (SU/FU) is equal to or greater than the ratio of the number of stiff units to flexible units in said Y segment (SU'/FU').

44. A polymer composition comprising lightly crosslinked linear molecules having the repeating structures prior to crosslinking of the general formula:

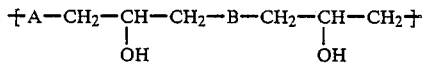

where A is selected from the group consisting of:

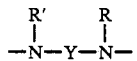

and mixtures thereof, and B is selected from the group consisting of:

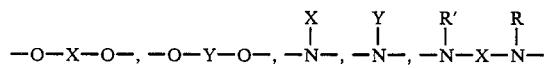

where R and R' are selected from the group consisting of unsubstituted or inertly substituted $C_1$-$C_{20}$ aliphatic, cycloaliphatic or aromatic hydrocarbyl groups, and wherein said repeating structures are lightly crosslinked such that between 1 and 50 of said repeating structures per 100 total repeating structures are crosslinked to repeating structures of other molecules, and where:
(a) "X" represents a segment comprising stiff units (SU) and optional flexible units (FU), which stiff units and flexible units are interconnected;
(b) "Y" represents a segment comprising stiff units (SU') and optional flexible units (FU') which stiff units and flexible units are interconnected;
(c) said stiff units, SU and SU', are independently selected from the group consisting of substituted and non-substituted benzene, naphthalene, anthracene and phenanthrene rings, and non-interfering heterocyclic rings;
(d) said flexible units, FU and FU', are independently selected from the group consisting of

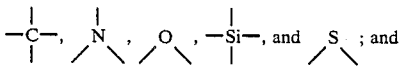

and (e) the ratio of the number of stiff units to flexible units in said X segment (SU/FU) is greater than the ratio of the number of stiff units to flexible units in said Y segment (SU'/FU').

45. A polymer composition comprising lightly crosslinked linear molecules having the repeating structures prior to crosslinking of the general formula:

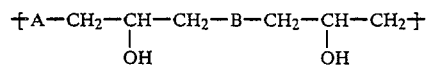

where A is selected from the group consisting of:

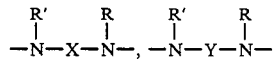

and mixtures thereof, and B is selected from the group consisting of:

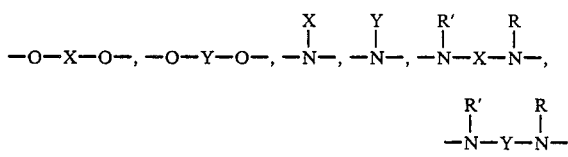

where R and R' are selected from the group consisting of unsubstituted or inertly substituted $C_1$-$C_{20}$ aliphatic, cycloaliphatic or aromatic hydrocarbyl groups, and wherein said repeating structures are lightly crosslinked such that between 1 and 50 of said repeating structures per 100 total repeating structures are crosslinked to repeating structures of other molecules, and where:
(a) "X" represents a segment comprising stiff units (SU) and optional flexible units (FU), which stiff units and flexible units are interconnected;
(b) "Y" represents a segment comprising stiff units (SU') and optional flexible units (FU') which stiff units and flexible units are interconnected;
(c) said stiff units, SU and SU', are independently selected from the group consisting of substituted and non-substituted benzene, naphthalene, anthracene and phenanthrene rings, and non-interfering heterocyclic rings;
(d) said flexible units, FU and FU', are independently selected from the group consisting of

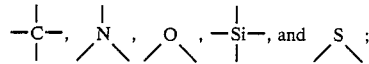

(e) the ratio of the number of stiff units to flexible units in said X segment (SU/FU) is equal to or greater than the ratio of the number of stiff units to flexible units in said Y segment (SU'/FU').

46. The composition according to any one of claim 1, 42, 43, 44 or 45 wherein the average number of total stiff units divided by the average number of total flexible units is equal to or greater than 2 and less than about 20.

47. The composition according to any one of claim 1, 42, 43, 44 or 45 wherein the ratio of $$\frac{SU}{FU} > \frac{SU'}{FU'} + 0.5.$$

48. The composition according to any one of claims 2, 42, 44 or 45 wherein B is selected from —O—X—O— and —O—Y—O—.

49. The composition of claim 48 wherein A is

and B is —O—X—O.

50. The composition according to any one of claims 1, 42, 43, 44 or 45 wherein between about one and about 99 mole percent of A is replaced with a group selected from the group consisting of —O—X—O— and —O—Y—O—.

51. The composition according to any one of claims 1, 42, 43, 44 or 45 wherein between about 25 and about 75 mole percent of A is replaced with a group selected from the group consisting of —O—X—O— and —O—Y—O—.

52. The composition according to any one of claims 1, 42, 43, 44 or 45 wherein the flexible unit is

53. The composition according to any one of claims 1, 42, 43, 44 or 45 wherein the flexible unit is

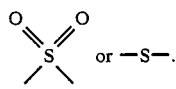

54. The composition according to any one of claim 1, 42, 43, 44, or 45 wherein the flexible unit is

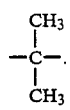

55. The composition according to any one of claim 1, 42, 43, 44 or 45 wherein the stiff unit is an aromatic ring selected from naphthalene, anthracene and phenanthrene.

56. The composition according to any one of claim 1, 42, 43, 44 or 45 wherein the stiff unit is a heterocyclic ring selected from pyrrole, furan, thiophene, imidazole, oxazole, thiazole, pyridine, dibenzothiophene, carbazole and malimide.

57. The composition according to claim 42 wherein said linear molecules are prepared by reacting a first component with a second component, said first component being a primary monoamine and said second component is a diepoxide of a biphenol.

58. The composition according to claim 57 wherein the diepoxide is α,α'-bis[1-2,3-epoxypropoxy)-2-naphthyl]-para-diisopropylbenzene.

59. The composition according to claim 57 wherein Z is

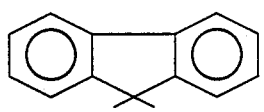

60. The composition according to claim 57 wherein Z is

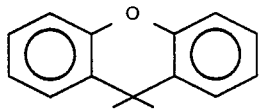

61. The composition according to claim 57 wherein the diepoxide is the diglycidyl ether of 9,9-bis(4-hydroxyphenyl)fluorene.

62. The composition according to claim 57 wherein the average number of total stiff units divided by the average number of total flexible units is greater than 4 and less than 20.

63. The composition according to claim 57 wherein the amine is an aromatic hydrocarbon amine.

64. The composition according to claim 63 wherein the amine is 2,6-dimethylaniline.

65. The composition according to claim 63 wherein the amine is 2,6-diethylaniline.

66. The composition according to claim 57 wherein the diepoxide is 4,4-bis(2,3-epoxypropoxy)biphenyl.

67. The composition according to claim 57 wherein a portion of the amine is replaced by a bisphenol which is 4,4'-dihydroxybiphenyl.

68. The composition according to claim 57 wherein a portion of the amine is replaced by a bisphenol which is 2,2-bis(4-hydroxyphenyl)propane.

69. The composition according to claim 57 wherein the bisphenol is

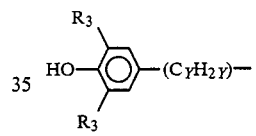

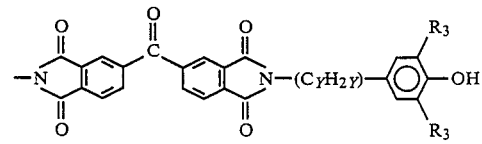

wherein each $R_3$ is the same or different $C_1$–$C_4$ alkyl and Y is 0 to 3.

70. The composition according to claim 57 wherein the average number of total stiff units divided by the average number of total flexible units is greater than 5 and less than 10.

71. The composition according to any one of claims 44 or 45 wherein said linear molecules are prepared by reacting a first component with a second component, said first component being bis secondary amines and said second component is a diepoxide of a bisphenol.

72. The composition according to claim 71 wherein the diepoxide is α,α'-bis[1(-2,3-epoxypropoxy)-2-naphthyl]-para-diisopropyl benzene.

73. The composition according to claim 71 wherein the average number of total stiff units divided by the average number of total flexible units is greater than 4 and less than 20.

74. The composition according to any one of claims 43, 44 or 45 wherein said linear molecules are prepared by reacting a first component with a second component, said first component being an aromatic hydrocarbon amine and said second component being a diepoxide of a bisphenol or of a bis secondary amine.

75. The composition according to claim 74 wherein the first component amine is N,N'-dimethyl-α,α'-bis(4-aminophenyl)-p-diisopropylbenzene.

76. The composition of claim 75 wherein said second component is α,α'-bis[1-(2,3-epoxypropoxy)-2-naphtyl]-para-diisopropylbenzene.

77. The composition of claim 76 wherein said crosslinking agent is a multifunctional amine of the formula

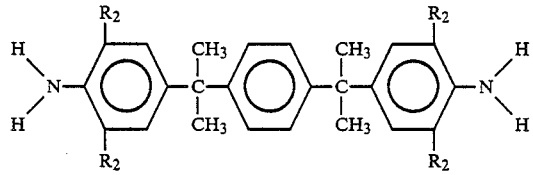

where R$_2$ is H or CH$_3$.

78. The composition according to claim 74 wherein the first component amine is N,N'-diethyl-α,α'-bis(4-aminophenyl)-p-diisopropylbenzene.

79. The composition according to claim 74 wherein the first component amine is α,α'-bis(4-aminophenyl)-p-diisopropylbenzene.

80. The composition according to claim 74 wherein the first component amine is N,N'-di-sec-butylbis(4-aminophenylmethane).

81. The composition according to claim 71 wherein the diepoxide is 4,4-bis(2,3-epoxypropoxy)biphenyl.

82. The composition according to claim 74 wherein a portion of the first component amine is replace by a bisphenol which is 4,4'-dihydroxybiphenyl.

83. The composition according to claim 74 wherein a portion of the first component amine is replaced by a bisphenol which is 2,2-bis(4-hydroxyphenyl)propane.

84. The composition according to claim 74 wherein a portion of the first component amine is replaced by a bisphenol which is

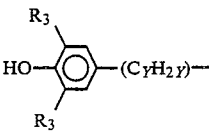

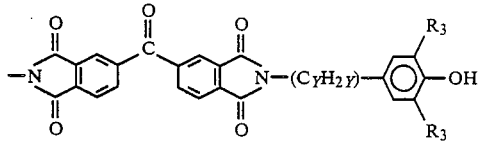

wherein each R$_3$ is the same or different C$_1$-C$_4$ alkyl and Y is 0 to 3.

85. The composition according to claim 74 wherein the average number of total stiff units divided by the average number of total flexible units is greater than 5 and less than 10.

86. The composition of claim 73 wherein said second component is α,α'-bis[1-(2,3-epoxypropoxy)-2-naphthyl]-para-diisopropylbenzene.

87. The composition of claim 86 wherein said first and second components are reacted in the presence of a crosslinking agent which is a multifunctional amine of the formula

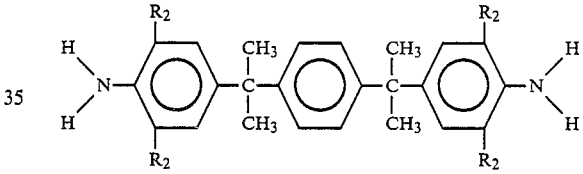

where R$_2$ is H or CH$_3$.

* * * * *